(12) United States Patent
Dargahi et al.

(10) Patent No.: US 8,596,111 B2
(45) Date of Patent: Dec. 3, 2013

(54) SYSTEM FOR SENSING AND DISPLAYING SOFTNESS AND FORCE

(75) Inventors: Javad Dargahi, Montreal (CA); Saeed Sokhanvar, Cambridge, MA (US)

(73) Assignee: Concordia University, Montreal (CA)

(*) Notice: Subject to any disclaimer, the term of this patent is extended or adjusted under 35 U.S.C. 154(b) by 189 days.

(21) Appl. No.: 12/988,410

(22) PCT Filed: Apr. 20, 2009

(86) PCT No.: PCT/CA2009/000529
§ 371 (c)(1),
(2), (4) Date: Jan. 6, 2011

(87) PCT Pub. No.: WO2009/127071
PCT Pub. Date: Oct. 22, 2009

(65) Prior Publication Data
US 2011/0107842 A1    May 12, 2011

Related U.S. Application Data

(60) Provisional application No. 61/071,247, filed on Apr. 18, 2008.

(51) Int. Cl.
*G01L 1/00* (2006.01)
(52) U.S. Cl.
USPC .................................. 73/78; 73/774; 73/780
(58) Field of Classification Search
USPC .............. 73/780, 78, 767, 774, 788, 862.391, 73/862.451, 862.541
See application file for complete search history.

(56) References Cited

U.S. PATENT DOCUMENTS

| | | | |
|---|---|---|---|
| 4,159,640 A | | 7/1979 | Leveque et al. |
| 4,266,263 A | * | 5/1981 | Haberl et al. ............... 361/283.2 |
| 4,539,554 A | * | 9/1985 | Jarvis et al. .................... 310/311 |
| 4,793,429 A | * | 12/1988 | Bratton et al. ............ 177/210 C |
| 4,821,584 A | * | 4/1989 | Lembke ...................... 73/862.68 |
| 5,524,636 A | | 6/1996 | Sarvazyan et al. |
| 5,661,245 A | * | 8/1997 | Svoboda et al. ................ 73/726 |
| 6,663,641 B1 | | 12/2003 | Kovac et al. |
| 6,848,304 B2 | | 2/2005 | Geen |
| 7,303,534 B2 | | 12/2007 | Kahn |

(Continued)

FOREIGN PATENT DOCUMENTS

JP    2005052212 A  *  3/2005  ............... A61B 5/00

OTHER PUBLICATIONS

English Translation of JP 2005-052212 A.*
Int'l Search Report PCT/CA2009/000529.

(Continued)

*Primary Examiner* — Hezron E Williams
*Assistant Examiner* — Alexander Mercado (57) ABSTRACT

A sensing element for sensing the softness of an object by abutting the sensing element against the object and biasing the sensing element toward the object with a biasing force. The sensing element includes a deformable section, the deformable section being deformable between an undeformed configuration and a deformed configuration, the deformed configuration being achievable when the deformable section is abutted against and biased toward the object; a deformation sensor operatively coupled to the deformable section for sensing a deformation of the deformable section between the deformed and undeformed configurations; and a force sensor operatively coupled to the deformable section for sensing the biasing force exerted onto the deformable section by the object when the deformable section is biased toward the object with the biasing force.

17 Claims, 9 Drawing Sheets

(56) References Cited

U.S. PATENT DOCUMENTS

| | | | |
|---|---|---|---|
| 7,357,036 B2* | 4/2008 | Steprath | 73/767 |
| 7,779,698 B2* | 8/2010 | Willcox | 73/716 |
| 2003/0176948 A1 | 9/2003 | Green | |
| 2004/0232201 A1 | 11/2004 | Wenchell et al. | |
| 2005/0065426 A1 | 3/2005 | Porat et al. | |
| 2005/0102062 A1 | 5/2005 | Green | |
| 2005/0131390 A1 | 6/2005 | Heinrich et al. | |
| 2005/0262949 A1 | 12/2005 | Schostek et al. | |
| 2006/0152885 A1 | 7/2006 | Hewit et al. | |
| 2009/0007684 A1* | 1/2009 | Kurtz et al. | 73/767 |
| 2012/0247192 A1* | 10/2012 | Diaz et al. | 73/78 |
| 2012/0274599 A1* | 11/2012 | Schediwy | 345/174 |
| 2013/0068038 A1* | 3/2013 | Bolender et al. | 73/862.626 |

OTHER PUBLICATIONS

Ashkan Mirbagheri et al., "Mathematical Modeling of a Tactile Sensor with Applications in Minimally Invasive Surgery", American Journal of Applied Sciences, Oct. 2007, vol. 4 (Issue 10), pp. 779-785.

Dargahi J. et al."Fabrication and testing of a medical surgical instrument capable of detecting simulated embedded lumps" American Journal of Applied Sciences, Dec. 2007, vol. 4, No. 12, pp. 957-964.

Dargahi J. et al. "Design and microfabrication of a hybrid piezoelectric-capacitive tactile sensor", Sensor Review, Sep. 2006 vol. 26, Issue 3; pp. 186-192.

Dargahi J. "An endoscopic and robotic tooth-like compliance and roughness tactile sensor" Journal of Mechanical Design, Sep. 2002, vol. 124, pp. 576-582.

Dargahi J. et al. "A micromachined piezoelectric tactile sensor for endoscopic grasper: theory, fabrication and experiments", IEEE-ASME Journal of MicroElectroMechanical Systems, Sep. 2000, vol. 9, No. 3, pp. 329-336.

Dargahi J., "A piezoelectric tactile sensor with three sensing elements for robotic, endoscopic and prosthetic applications", Sensors and Actuators A: Physical, Mar. 2000, vol. 80/1, pp. 23-30.

* cited by examiner

SYSTEM FOR SENSING AND DISPLAYING SOFTNESS AND FORCE

FIELD OF THE INVENTION

The present invention relates to the art of remote sensing. More specifically, the present invention is concerned with systems for sensing and displaying softness. In some embodiments of the invention, the invention is also concerned with systems for sensing and displaying force.

BACKGROUND OF THE INVENTION

The sense of touch provides essential feedback to surgeons performing interventions. For example, this type of feedback can help a surgeon in discriminating between different tissues, or to locate within a given tissue a specific portion on which an intervention must be performed or, conversely, on which accidental manipulations should be avoided.

There has been a move in recent years toward minimally invasive surgeries. In this type of surgery, a surgical instrument is inserted through a relatively small opening, or a blood vessel, in the body of a patient. This deprives the surgeon from direct access to the tissues and, therefore, greatly diminishes the quantity and quality of information that is available to the surgeon, such as tactile feedback. Also, there have been many attempts to develop systems for remotely performing surgery using robots. Once again, in these types of systems, tactile feedback is not provided to the surgeons.

There have been attempts to provide devices for restoring, at least in part, this feedback. For example, some surgical tools include force sensors that can sense the force exerted between the two jaws of a grasper. At the other end of the tool, handles operated by the surgeon are attached to actuators that reproduce the forces sensed by the grasper. However, these types of devices can provide only force feedback; in addition they are not able to discriminate spatially over the tissue grasped between the two jaws of the grasper. Also, only relatively crude measurements are provided and, therefore, only a relatively crude feedback is provided to the surgeon.

The need to measure contact force and the softness of the tissue is also seen in catheter based surgery. Indeed, in this type interventions, surgeons often needs to know how much force is applied to a tissue by the tip or body of a catheter. In addition, integration of softness sensing to such applications can help in differentiating tissues. While some techniques are already used in some systems to sense the softness of tissues, for example optic based techniques, such techniques are inefficient in applications in which there is blood flow. For example, in anuloplasty heart surgery, differentiating leaflet tissues from surrounding tissues and finding suitable locations to insert the anchor is a critical to success of the intervention.

Accordingly, there is a need in the industry to provide an improved system for sensing and displaying softness and force. An object of the present invention is therefore to provide such a system.

SUMMARY OF THE INVENTION

In a broad aspect, the invention provides a sensing element for sensing the softness of an object by abutting the sensing element against the object and biasing the sensing element toward the object with a biasing force. The sensing element includes a deformable section, the deformable section being deformable between an undeformed configuration and a deformed configuration, the deformed configuration being achievable when the deformable section is abutted against and biased toward the object; a deformation sensor operatively coupled to the deformable section for sensing a deformation of the deformable section between the deformed and undeformed configurations; and a force sensor operatively coupled to the deformable section for sensing the biasing force exerted onto the deformable section by the object when the deformable section is biased toward the object with the biasing force.

Advantageously, the proposed sensing element, by measuring the force exerted onto the deformable section as well as the deformation of the deformable section, can calibrate in absolute value the softness of the object. In some embodiments of the invention, the proposed sensing element is manufacturable relatively easily using well-known micro manufacturing technology.

The force and deformation are sensed using any suitable technique, such as piezoelectric, piezoresistive, capacitive, inductive or optical techniques, among others.

In some embodiments of the invention, an array of sensing elements is provided, the sensing elements being disposed in a side by side relationship relatively to each other. The array of sensing elements therefore provides a softness sensor allowing for the formation of an image of the softness of the object.

In some embodiments of the invention, the sensing element is included in a system for sensing and displaying softness. In such a system, the softness sensor as described hereinabove is coupled to a softness display. The softness display includes a plurality of display elements, each display element including an individually actuated pin that can exert a predetermined force onto the hand or fingers of an intended user of the softness display or which, conversely, can detect the force exerted on the pin and move the pin accordingly to reproduce a predetermined force-displacement relationship representative of the object. The object can be either a modelled object for which a model has been computed, or a real object for which the softness has been sensed using the softness sensor in a substantially real-time fashion.

Although the present patent application often make references to application in the field of robotic surgery, the devices and methods of the present application also have many other applications. For example, force, softness and temperature sensing and displaying systems have many potential applications in the gaming industry and, more generally, in computer or hand held gaming devices, as well as in virtual-reality systems. Furthermore, the systems presented in the present application are usable in many hostile environmental conditions, such as, for example, in space exploration. Indeed, tactile feedback is of paramount importance in the performance of many tasks, but protective gear often reduces such feedback. Also, in very hostile environments, robotic systems are used, which could also benefit greatly from the present invention.

Other objects, advantages and features of the present invention will become more apparent upon reading of the following non-restrictive description of preferred embodiments thereof, given by way of example only and in relation with the following Figures.

BRIEF DESCRIPTION OF THE DRAWINGS

FIG. 5, in a schematic cross-sectional view taken along the line X-X of FIG. 4, illustrates the softness sensor of FIG. 4;

FIG. 7C, in a schematic perspective view with portions removed, illustrates the softness sensor shown in FIGS. 6, 7A and 7B;

DETAILED DESCRIPTION

The invention relates to a system for sensing and displaying softness. Although, in some embodiments of the invention, the system includes both a softness sensor 10, shown for example in FIG. 1, and a softness display 14, shown for example in FIG. 10, in other embodiments of the invention only one of the softness sensor 10 and the softness display 14 is used. The softness sensor 10 can also be coupled with any other suitable softness display. The softness sensor 10 and the softness display 14 are operatively coupled to each other such that the softness sensed by softness sensor 10 can be displayed by the softness display 14. Typically, this is done by including a general purpose computer to which both the softness sensor 10 and the softness display 14 are connected. However, in some embodiments of the invention, specialized hardware is used to interconnect the softness sensor 10 and the softness display 14. Such computers and hardware are well known in the art and will therefore not be described in further details.

When only the softness sensor 10 is used, alternative means of collecting and displaying the data shown by the softness sensor 10 are used. For example, these alternative means may include a computer including a data acquisition card that is usable to acquire the electrical signals produced by the softness sensor 10 and display them, for example graphically or as numerical values values presented in numeric characters, among other possibilities.

Also, in some embodiments of the invention, the softness display 14 is usable without having the softness sensor 10 directly connected to the system. In these embodiments, either previously acquired data that has been acquired using the softness sensor 10 is used to drive the softness display 14, or an object for which softness is to be displayed is modelled, once again, using methods that are well known in the art.

Figure 1:
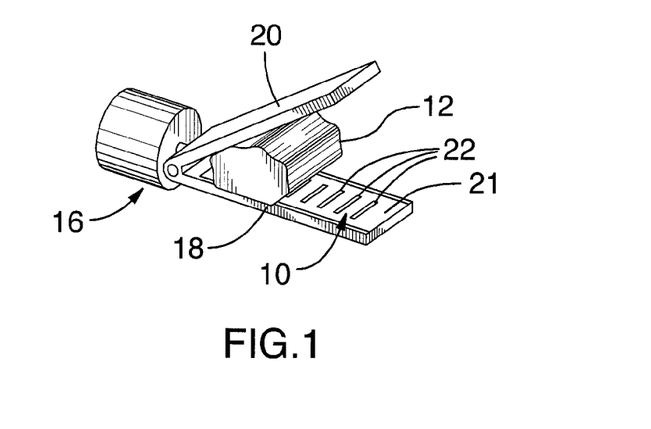
FIG. 1, in a perspective view, illustrates a grasper including a softness sensor for sensing the softness of an object in accordance with an embodiment of the present invention.

A specific example of an embodiment of the softness sensor 10 is illustrated in FIG. 1. The softness sensor 10 is part of a grasper 16 that is usable for grasping an object 12. For example, the grasper 16 includes two jaws 18 and 20 that are pivotally connected to each other. Using a conventional actuating mechanism (not shown in the drawings), an intended user may grasp the object 12 between the two jaws 18 and 20 such that the object 12 is biased toward the two jaws 18 and 20 by a biasing force.

One of the jaws, more specifically in the drawings the jaw 18, includes a softness sensor 10. The softness sensor 10 includes sensing elements 22 distributed over a predetermined sensing surface 21. For example, in the embodiment shown in FIG. 1, the sensing elements 22 are in a side by side relationship relatively to each other along a substantially rectilinear configuration defining a longitudinal direction. In this embodiment, the predetermined sensing surface 21 is substantially planar. However, other configurations of the predetermined sensing surface 21 are within the scope of the present invention.

Using an array of sensing elements 22, the position of the object with respect to the grasper 16 can be determined. In addition, slippage of the object 12 with respect to the grasper 16 can be also detected. However, other configurations for the sensing elements 22 are within the scope of the invention such as, for example, two-dimensional arrays of sensing elements 22, and sensing elements 22 disposed in concentric circles relatively to each other, among other possibilities. Also, by including sensing elements 22 in both jaws 18 and 20, more information about the object 12 can be obtained. For instance, information about the size, depth and softness of a hidden anatomical feature can be obtained.

Figure 12:
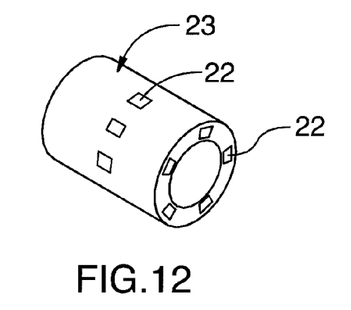
FIG. 12, in a perspective view, illustrates a tip portion of a catheter including the sensing elements illustrated in FIGS. 2 to 7.

As shown in FIG. 12, in some embodiments of the invention, the sensing elements 22 are provided on the outer surface of a catheter 23 insertable in a patient (not shown in the drawings). The sensing elements 22 can be provided at the tip of the catheter 23, on the lateral outer surface of the catheter 23, for example substantially adjacent the tip of the catheter 23, or both on the lateral outer surface and tip of the catheter 23.

Figure 2:
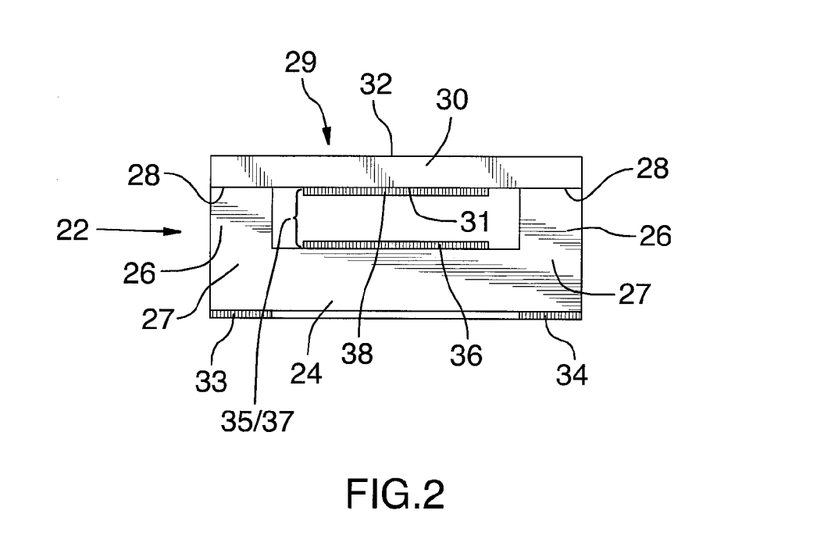
FIG. 2, in a schematic side cross-sectional view, illustrates the softness sensor of FIG. 1 in accordance with an embodiment of the present invention.

FIG. 2 illustrates, in a side cross-sectional view, one of the sensing elements 22 shown in FIG. 1. Generally speaking, each sensing element 22 is used for sensing the softness of the object 12 by abutting the sensing element 22 against the object 12 and biasing the sensing element 22 toward the object 12 with a biasing force. The sensing element 22 includes a deformable section 29, the deformable section 29 being deformable between an undeformed configuration (shown in FIG. 2) and a deformed configuration (shown in FIGS. 3A and 3B), the deformed configuration being achievable when the deformable section 29 is abutted against and biased toward the object 12. A deformation sensor 35 is operatively coupled to the deformable section 29 for sensing a deformation of the deformable section 29 between the deformed and undeformed configurations. A force sensor 33, 34 is operatively coupled to the deformable section 29 for sensing the biasing force exerted onto the deformable section 29 by the object 12 when the deformable section 29 is biased toward the object with the biasing force.

The sensing element 22 includes a base 24. Two spacing elements 26 extending substantially away from the base 24 are provided for supporting the deformable section 29, the deformable section 29 extending between the spacing elements 26 and being supported by the spacing elements 26 in a substantially spaced apart relationship relatively to the base 24. Typically, the spacing elements 26 extend from the base 24 in a laterally spaced apart relationship relatively to each other. While a sensing element 22 including a pair of spacing elements 26 is shown in the drawings, in some embodiments of the sensing element 22 includes a single spacing element 26, and the deformable section 29 is supported in a cantilevered configuration in a substantially spaced apart relationship relatively to the base 24.

Each of the spacing elements 26 defines a respective spacing element proximal end 27 and a substantially opposed respective spacing element distal end 28. The spacing element distal end 28 is spaced apart from the base 24 and the spacing element proximal end 27 is located between the base 24 and the spacing element distal end 28. In the embodiment of the invention shown in FIG. 2, the spacing element proximal end 27 is adjacent the base 24 and the spacing elements 26 therefore extend integrally from the base 24.

The deformable section 29 defines a deformable section distal end 32 located in a substantially spaced apart relationship relatively to the base 24 and a deformable section proximal end 31 located between the base 24 and the deformable section distal end 32. In the deformed configuration, the deformable section proximal end 31 is closer to the base 24 than in the undeformed configuration. In the embodiment of the invention shown in FIG. 2, the deformable section 29 includes a beam 30 extending between the two spacing elements 26. The beam 30 is spaced apart from the base 24 by the two spacing elements 26 such that, when the beam 30 is deformed, a central section of the beam 30 is moved toward the base 24.

Two force sensors 33 and 34 are mechanically coupled to the spacing elements 26 for sensing a force exerted on the spacing elements 26 when the deformable section is abutted against and biased toward the object. More specifically, the two force sensors 33 and 34 are operatively coupled each to a respective one of the two spacing elements 26 for sensing a force exerted on the spacing elements 26 when the deformable section 29 is abutted against and biased toward the object for sensing a force exerted by the object 12 onto a respective one of the two spacing elements 26.

For example, and non-limitingly, each force sensor 33, 34 includes a piezoelectric material operatively coupled to the spacing elements 26 for producing an electrical signal upon a force being exerted on the spacing elements 26. In the embodiment of the invention shown in the drawings, a piezoelectric film is attached to the base 24 substantially opposite to the spacing elements 26. An example of such a piezoelectric film is a polyvinylidene fluoride (PVDF) film. When forces are exerted onto the spacing element 26, the piezoelectric film of the force sensors 33 and 34 produces electrical signals that are conveyed to a data acquisition apparatus for acquiring these electrical signals. The use of two force sensors 33 and 34 enables the sensing element 22 to register the position of a point load applied along the deformable section 29. For clarity reasons, these electrodes and wires that are used to receive the electrical signals provided to the electrodes are not shown in the drawings, but the reader skilled in the art will readily appreciate which configurations of electrodes and wires would provide satisfactory signal acquisition.

A deformation sensor 35 is operatively coupled to the deformable section 29 for sensing a deformation of the deformable section 29 between the deformed and undeformed configurations. For example, the deformation sensor 35 includes a capacitor 37 operatively coupled to the deformable section 29 and to the base 24 for producing an electrical signal upon a deformation of the deformable section 29 between the deformed and undeformed configurations. The capacitor 37 includes a first metal plate 36 secured to the base 24 and a second metal plate 38 secured to the deformable section 29, the first and second metal plates 36 and 38 being substantially in register with each other. For example, the first and second metal plates 36 and 38 are located in the empty space provided between the beam 30 and the base 24. The first metal plate 36 is mechanically coupled to the base 24 and the second metal plate 38 is mechanically coupled to the beam 30 so as to be substantially jointly movable and deformable therewith.

The deformation sensor 35 provides measurements of the deflection, or stretch of the beam 30. FIG. 2 shows an example of such a deformation sensor 35 in which the deformation sensor 35 provides a measurement of the distance between the first and second metal plates 36 and 38, which is indicative of the deformations of the beam 30, through capacitance measurements. Once again, wires that are usable for effecting such a measurement are not shown in the drawings and specific configurations of these wires and other electronic components necessary for this capacitance measurement are conceivable easily by the reader skilled in the art and are therefore not described in further details.

Figure 3A:
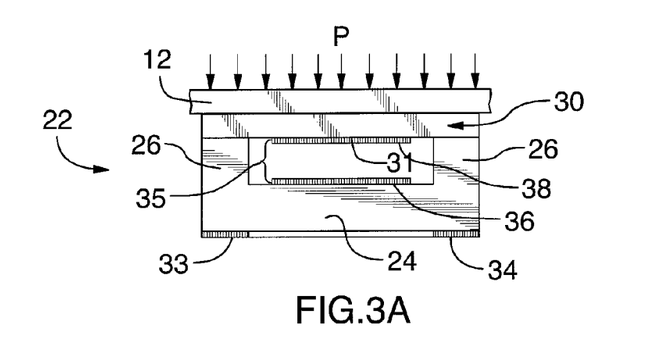
FIG. 3A, in a schematic side cross-sectional views, illustrates the deformation of the softness sensor of FIG. 2 in response to the exertion of a force thereonto by a hard object.
Figure 3B:
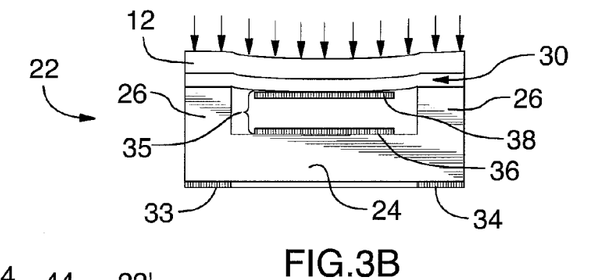
FIG. 3B, in a schematic side cross-sectional views, illustrates the deformation of the softness sensor of FIG. 2 in response to the exertion of a force thereonto by a soft object.

FIGS. 3A and 3B illustrate a manner in which the sensing element 22 can detect the softness of an object. In FIG. 3A, a relatively hard object 12 is biased against the sensing element 22. More specifically, the object 12 extends between the two spacing elements 26 and also contacts the beam 30. When the object 12 is relatively hard, exerting a relatively uniform force onto the object 12 will result in relatively small deformations of the object 12. Accordingly, the beam 30 will be deformed only to a relatively small extent and a distance between the first and second plates 36 and 38 will be relatively similar to a distance between the first and second metal plates 36 and 38 when the beam 30 is undeformed. When a similar force is exerted onto a relatively soft object 12, as shown in FIG. 3B, the object 12 will deform to a relatively large extent. In turn, this will deform the beam 30 such that the first and second metal plates 36 and 38 get closer to each other, thereby changing the capacitance between the first and second metal plates 36 and 38. Using the value of the force exerted onto the two spacing elements 26 provided by the force sensors 33 and 34 and the deformation of the beam 30 measured using the capacitance between the first and second metal plates 36 and 38, the softness of the object 12 can be modelled by considering the deformation characteristics of each component of the sensing element 22.

In some embodiments of the invention, the spacing elements 26 and the base 24 are integrally formed in silicon. Also, the beam 30 can also be made out of silicon or any other suitable material. Typically, it is desirable that the beam 30 be relatively easily deformable so as to provide good sensibility to the softness of different objects 12.

Figure 4:
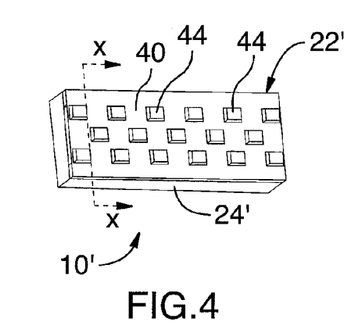
FIG. 4, in a perspective view, illustrates a softness sensor in accordance with an alternative embodiment of the present invention.
Figure 5:
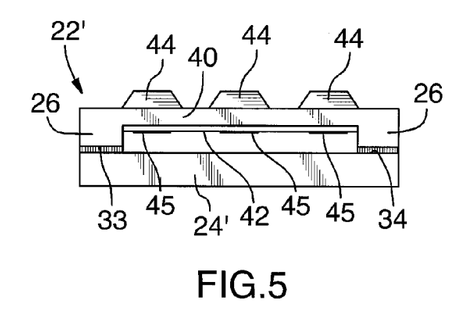
Figure 6:
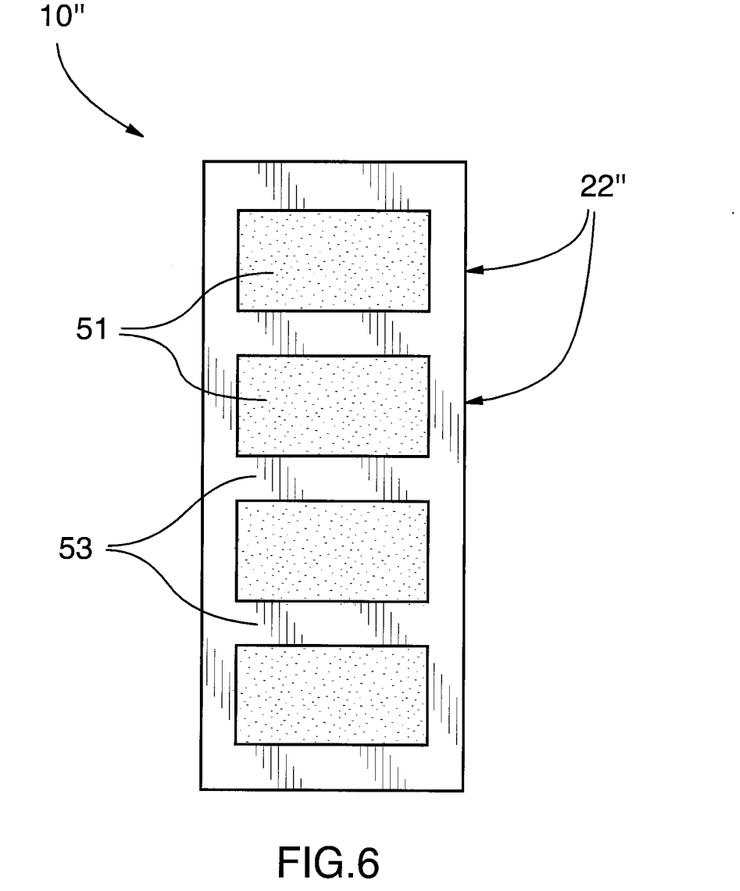
FIG. 6, in a top schematic view, illustrates a softness sensor in accordance with another alternative embodiment of the present invention.

FIGS. 4 and 5 illustrate an alternative softness sensor 10' including an alternative sensing element 22'. As seen in FIG. 5, the softness sensor 10' includes a substantially rigid base 24', for example made out of silicon. Force sensors 33 and 34 are provided between each of the spacing elements 26 and the base 24'. A membrane 40 extends between the spacing elements 26. A deformation sensor 42, for example a film of a piezoelectric material, is fixed to the membrane 40 for detecting deformations thereof.

The deformation sensor 42 includes a piezoelectric material operatively coupled to the membrane 40 for producing an electrical signal upon a deformation of the deformable section from which the membrane 40 is part of between the deformed and undeformed configurations. Teeth 44 extend from the membrane 40 substantially away from the base 24'.

The deformation sensor 42 also includes metal electrodes 45 electrically coupled to the piezoelectric material 43 for detecting a local or a global deformation of the deformation sensor 42. The reader skilled in the art will readily appreciate that, by having an array of metal electrodes 45 disposed over the surface of the deformation sensor 42, the metal electrodes 45 being electrically insulated from each other, local deformation of the deformation sensor 42 can be measured which, in turn, provides discrete sensing elements for measuring the softness of the object 12.

Also, only a specific embodiment of the deformation sensor 42 and the force sensors 33 and 34 has been presented herein above. Indeed, it is also possible in alternative embodiments of the invention to replace the deformation sensor 42 and force sensors 33 and 34 by deformation and deformation sensors using capacitive, inductive, optical, piezoelectric, piezoresistive and pressure sensitive material based techniques, among other possibilities. The deformable portion can have any suitable transversal cross-section, such as a trapezoidal, circular, rectangular or any other suitable cross-section. Also, the portion of the membrane 40 that abuts against the object 12 can have a substantially flat configuration, or can have protrusions protruding substantially upwardly therefrom for penetrating to the object 12 or gripping slippery objects 12.

The teeth 44, for example, have a frusto-pyramidal shape and serve to better grip the object 12, as well as to transmit locally the deformation of a specific portion of the object 12. Therefore, typically, each metal electrode 45 is disposed on the membrane 40 at a location substantially in register with a respective one of the teeth 44 and has similar dimensions to that specific tooth 44.

FIGS. 6 and 7A-7C illustrate a softness sensor 10" in accordance with another embodiment of the present invention. Materials and dimensions specified on these Figures are provided for example purposes and softness sensors 10" made out of other materials and having other dimensions are within the scope of the present invention.

The softness sensor 10" includes four substantially linearly aligned sensing elements 22". As better shown in FIGS. 7A-7C, a base 24, for example made out of glass or silicon, is substantially plate-shaped. Onto this base 24, a first metal electrode 48 is disposed. Then, a piezoelectric material layer 46 is disposed onto this first electrode 48. On the other side of the piezoelectric material layer 46, alternating electrodes 50 and 52 are disposed in a side-by-side relationship relatively to each other. Over each of the electrodes 50, a relatively soft material 51, such as for example liquid silicone rubber, is deposited. Over each of the electrodes 52, a relatively hard material 53, such as for example silicon, is deposited. In an alternative approach, a recess 57 is formed, for example, by etching silicon to be subsequently substantially filled with a deformable material, such as the relatively soft material 51. The base 24 includes a base material delimiting the recess 57. The relatively soft material 51 is substantially more deformable than the relatively hard material 53 when the relatively soft material 51 and the relatively hard material 53 are simultaneously abutted against and biased toward the object 12 (not shown in FIGS. 7A-7C).

Therefore, when the object 12 is abutted against and biased toward the softness sensor 10", different forces will be exerted onto the piezoelectric material layer 46 at different locations therealong, and, using the electrodes 50 and 52, these different forces can be determined. Since a relatively soft object 12 (not shown in FIGS. 6 and 7A-7C) will deform to a relatively large extent over the relatively soft material 51 of the softness sensor 10", this relatively soft object 12 will produce a larger force onto the piezoelectric material layer 46 and, will therefore produce a larger current as measured by each of the electrodes 50 than relatively harder objects 12.

Figure 7A:
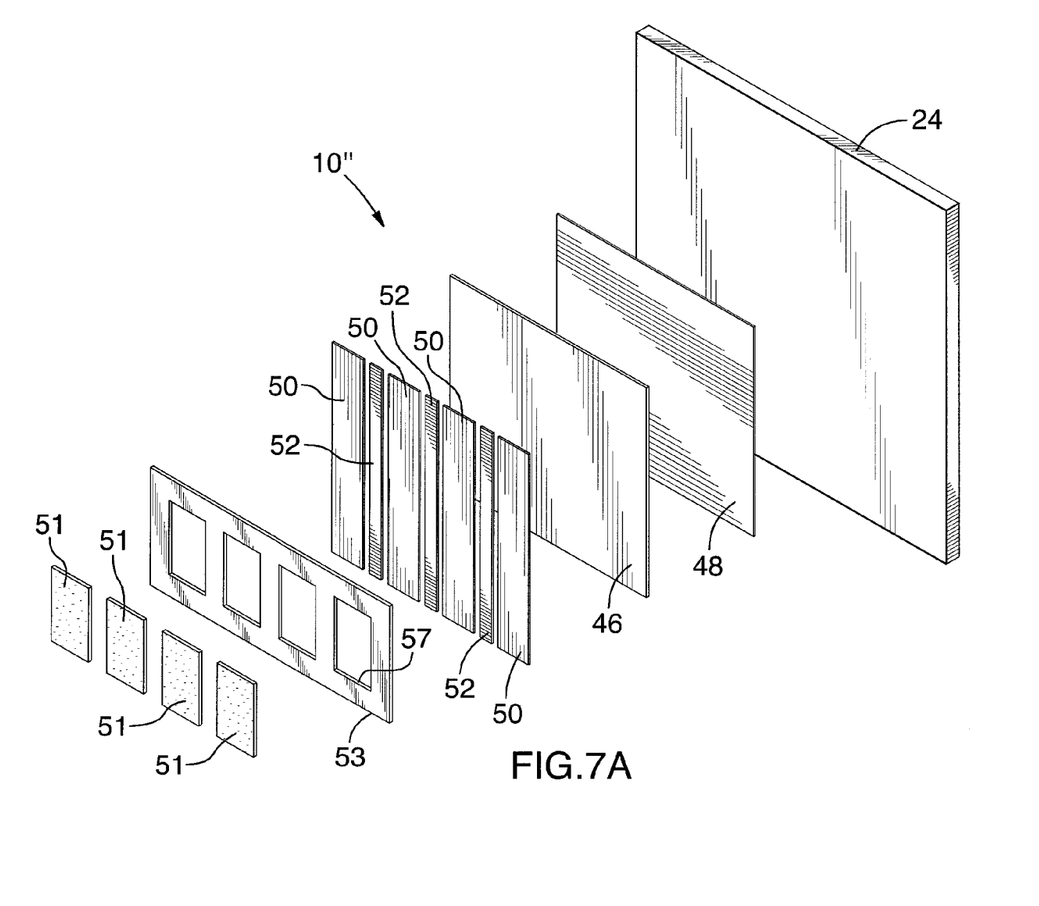
FIG. 7A, in a schematic perspective exploded view, illustrates the softness sensor shown in FIG. 6.
Figure 7B:
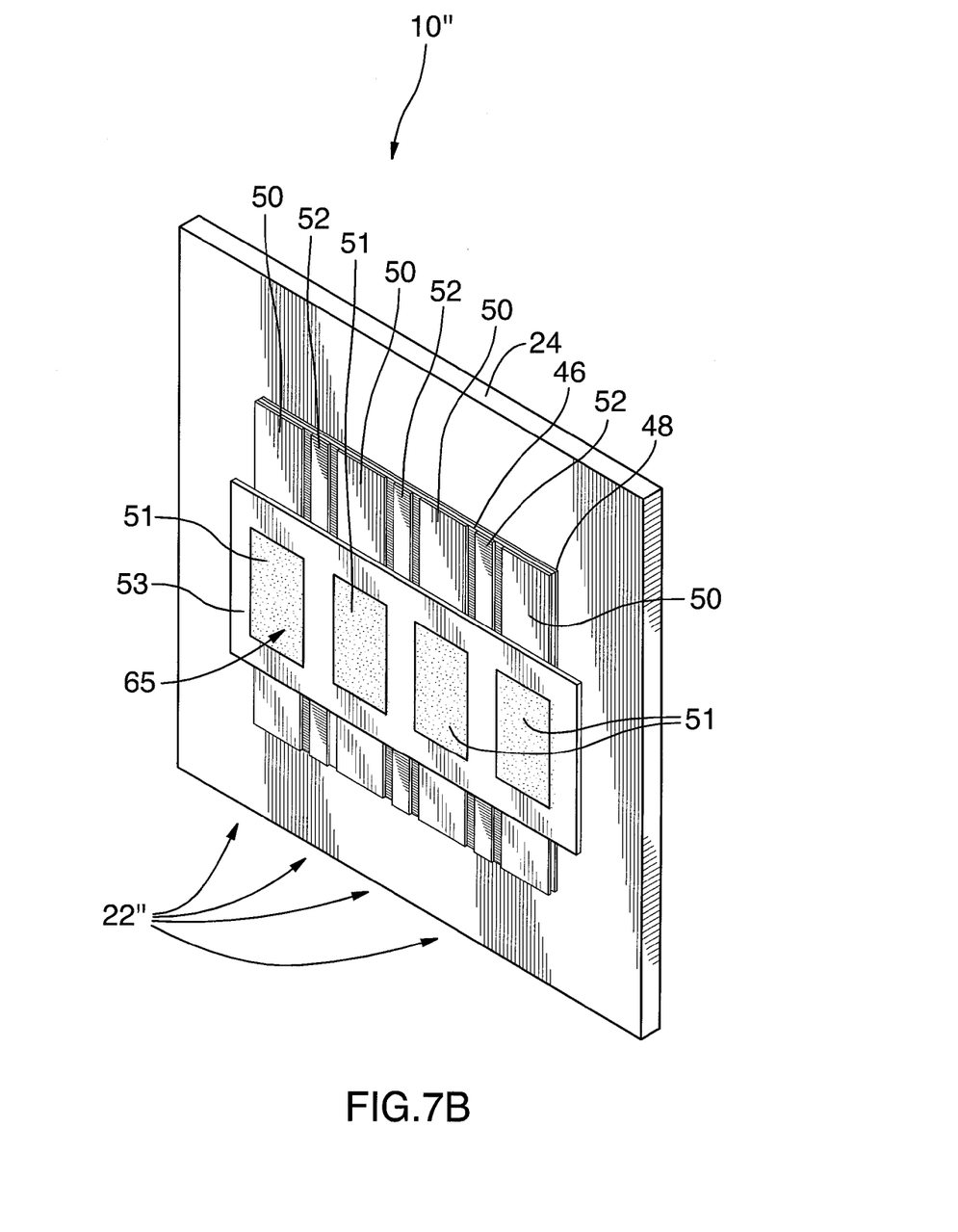
FIG. 7B, in a schematic perspective view, illustrates the softness sensor shown in FIGS. 6 and 7A.
Figure 7C:
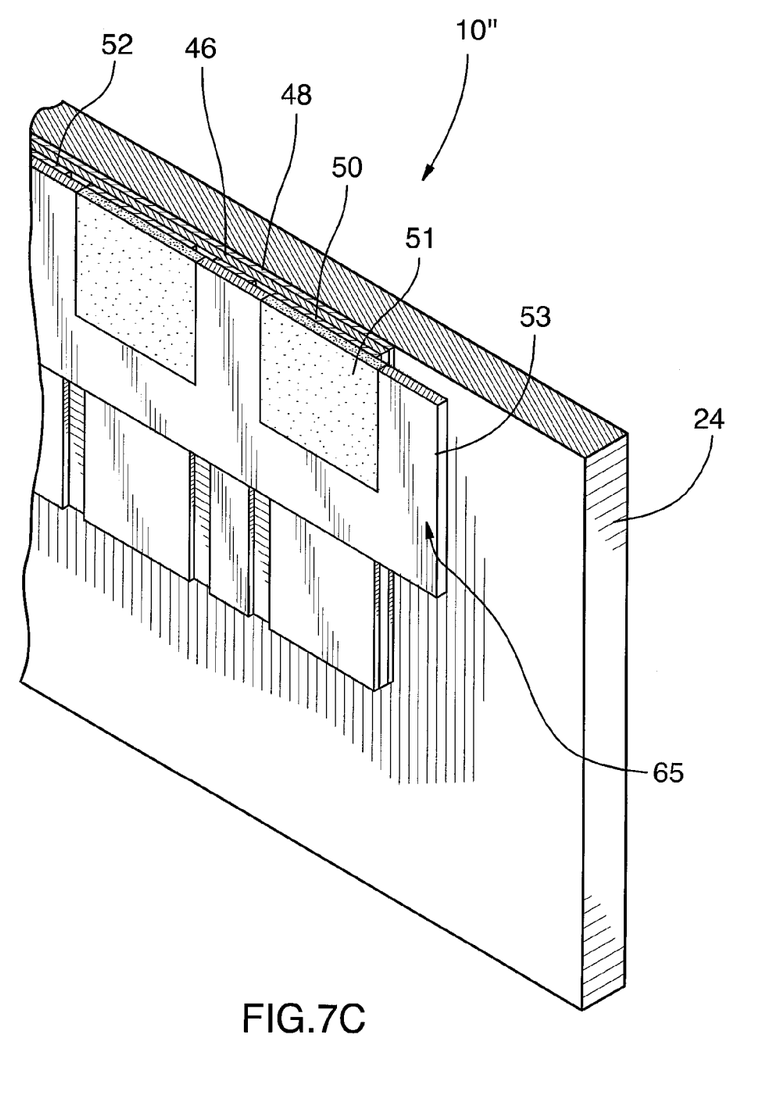

For example, in some embodiments of the invention, the electrodes 48, 50 and 52 are made out of aluminum. These electrodes 48, 50 and 52 are each connected to metal wires (not shown in the drawings) for conveying electrical signals produced inside the electrodes 48, 50 and 52 in response to forces being exerted onto the piezoelectric material layer 46. Therefore, the force sensor of the sensing elements 22" includes a piezoelectric material mechanically coupled to the relatively hard material 53 and to the deformable section for sensing forces exerted onto the relatively soft material 51 and the relatively hard material 53 when the relatively soft material 51 and the relatively hard material 53 are simultaneously abutted against and biased toward the object.

In other words, the relatively hard material 53 and the deformable section, and more specifically the relatively soft material 51, together define an abutment surface 65 for abutting against the object, the sensing element 22" comprising a sheet of piezoelectric material, the piezoelectric material layer 46, mechanically coupled to both the relatively soft material 51 and the relatively hard material 53 substantially opposed to the abutment surface 65.

The piezoelectric material layer 46 and the electrodes 50 are part of a deformation sensor. The electrodes 50 are therefore deformation sensor electrodes 50 electrically coupled to the piezoelectric material layer 46 for receiving electrical signals from the piezoelectric material layer 46 when a force is exerted onto the relatively soft material 51. The piezoelectric material layer 46 and the electrodes 52 are part of a force sensor. The electrodes 52 are therefore force sensor electrodes 50 electrically coupled to the piezoelectric material layer 46 for receiving electrical signals from the piezoelectric material layer 46 when a force is exerted onto the relatively soft material 51.

In addition to softness sensing, the above described softness sensors 10, 10' and 10", are usable for acquiring other characteristics of the object 12. For example, if the object 12 is pulsating, as is the case in arteries, these softness sensors 10, 10' and 10" are capable of sensing the pulsation amplitude and period. Indeed, any pulsed moving of the object 12 causes deformations of the deformation sensors and these deformations can also be displayed using softness of display 14.

Furthermore, recording the time dependency of the deformation sensors 35 can provide information on time dependent deformations of the object 12, and therefore allow analyzes of the viscoelastic and other time dependent behavior of the object 12.

Figure 8:
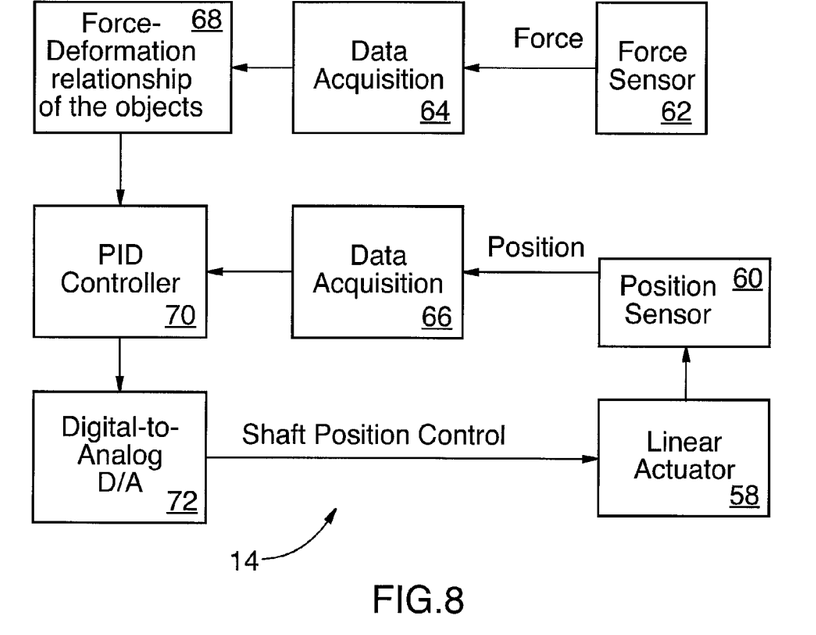
FIG. 8, in a schematic view, illustrates a softness display usable with the softness sensors shown in FIGS. 1 to 7.
Figure 9:
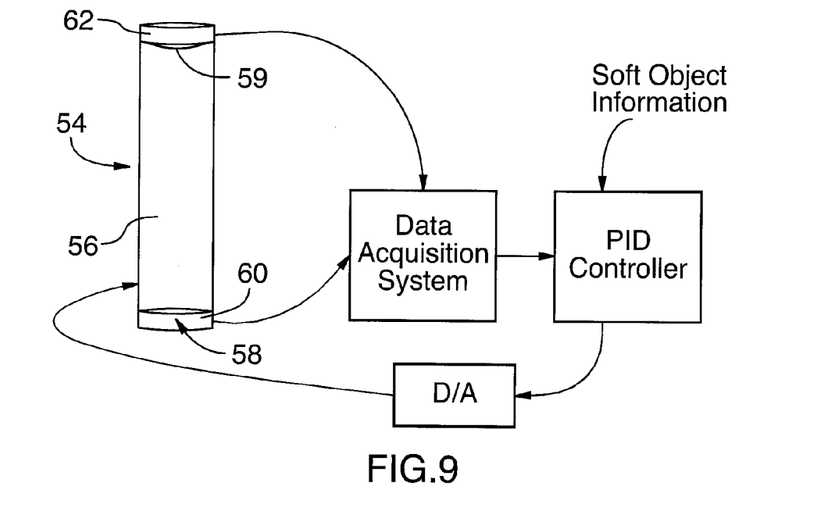
FIG. 9, in a schematic view, illustrates a display element included in the softness display of FIG. 8.
Figure 10:
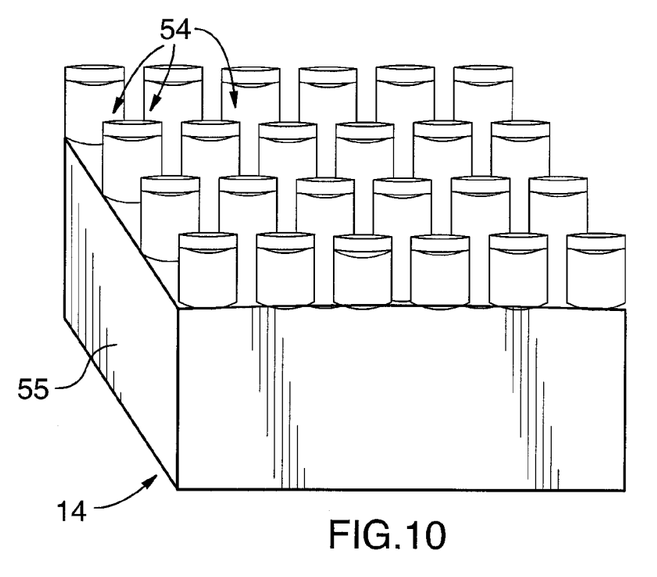
FIG. 10, in a schematic view, illustrates the geometry of the softness display of FIG. 8.

FIGS. 8 to 11 illustrate a softness display 14 in accordance with an embodiment of the present invention. Referring to FIG. 10, the softness display 14 includes display elements 54 disposed in an array configuration and mounted in a casing 55. The display elements 54 are each individually actuatable to convey the local softness of the object 12 (not shown in FIGS. 8 to 11).

More specifically, as seen in FIG. 9, each of the display elements 54 includes a pin 56 mounted to an actuator 58, the pin 56 defining a tip 59. The actuator 58 is, for example, a linear motor and moves the pin 56 longitudinally. The actuator 58 typically includes a position sensor 60 for sensing a position of the pin 56 relatively to the actuator 58. Also, a force sensor 62 is operatively coupled to the pin 56 for sensing a force exerted longitudinally onto the pin 56. For example, the force sensor 62 is a piezoelectric sensor disposed at the tip 59 of the pin 56. However, in alternative embodiments of the invention, the position and force sensors 60 and 62, as well as the actuator 58, take any other suitable form. Typically, each of the display elements 54 has relatively small dimensions so as to be able to convey onto the hand or fingers of an intended user the softness characteristics of an object.

Referring to FIG. 8, there is shown a schematic view of the softness display 14. The softness display 14, in addition to the display elements 54, includes a controller for controlling the actuators 58 to move the pins 56 in response to signals conveyed by the position and force sensors 60 and 62. The controller includes both a force acquisition module 64 and a position acquisition module 66. The force and position acquisitions modules 66 and 64 are respectively operatively coupled to the position sensor 60 and force sensors 62 of all the display elements 54 for receiving longitudinal forces exerted onto the pin 56 and the position of the pin 56 relatively to the actuator 58.

Figure 11:
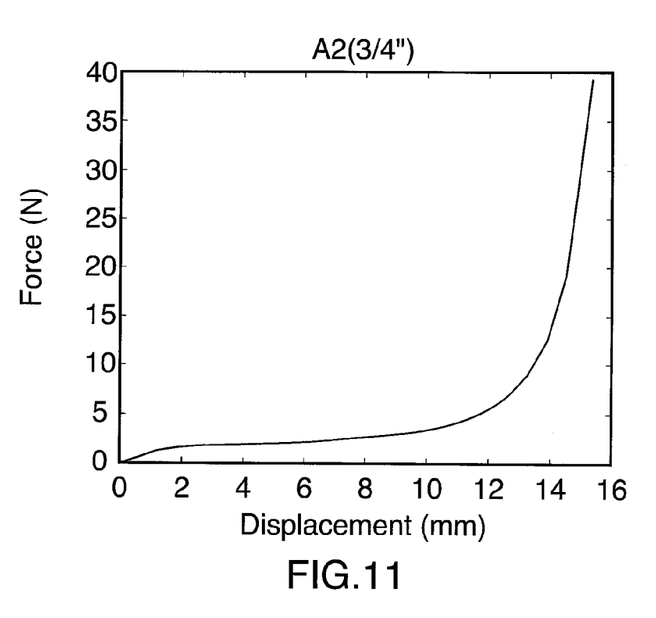
FIG. 11, in an X-Y graph, illustrates a force displacement curve usable to model an object in the softness display of FIGS. 8 to 10.

The force and position data acquired by the position and force acquisition modules 66 and 64 are sent respectively to an object modelling module 68 and to a pin position controller 70. More specifically, the force acquired by the force sensor 62 is conveyed to the object modelling module 68, which includes a model of an object for which softness is to be displayed. The object modelling module 68 includes force displacement characteristics for each of the positions represented by individual display elements 54, as seen, for example, in FIG. 11. It should be emphasized that the softness of each position corresponding to each display elements 54 is individually configurable so as to produce a softness image. Also, the force displacement characteristic is not necessarily linear, as shown in FIG. 11 and may, in some embodiments of the invention, even include hysteresis effects. This force displacement characteristic is either a force displacement characteristic modelled using a physical model of an object or a force displacement characteristic modelled using data acquired from the real object in real-time applications, for example using the softness sensor 10.

The object modelling module 68 determines the position that should be assumed by each of the pins 56 in response to the force measured by the force sensor 62 associated with this pin 56. Using the actual position of the pin 56 measured by the position sensor 60, and the desired position of the pin 56 received from the object modelling module 68, the pin position controller 70 outputs a signal to an output module 72 for displacing the pin 56 using the actuator 58 to the desired position. The output module 72 is operatively coupled to the actuators 58 of all the display elements 54 for sending control signals conveying information related to the position that should be assumed by each of the pins 56.

For example, in some embodiments of the invention, the pin position controller 70 is simply a P.I.D. controller used to position the pins 56 in a manner that is well known in the art. However, any other type of controller is usable in alternative embodiments of the invention.

In some embodiments of the invention, the force-displacement curve produced by the object modelling module is distorted such that softness differences between different portions of an object are enhanced. For example, the relatively hard lumps in relatively soft objects can be represented as almost incompressible lumps which, in some embodiments of the invention, can enhance the tactile feedback provided by the display elements 54. Also, in some embodiments of the invention, the display elements 54 are not disposed in a scale model of the object to represent, and the softness display 14 can therefore be used to display the softness of relatively small or relatively large objects using the same display element.

Figure 13A:
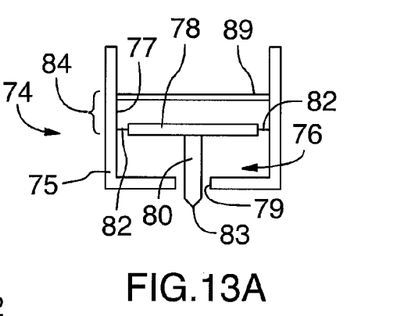
FIG. 13A, in a schematic view, illustrates a softness sensor in accordance with yet another embodiment of the present invention, the softness sensor being shown in an undeformed configuration.
Figure 13B:
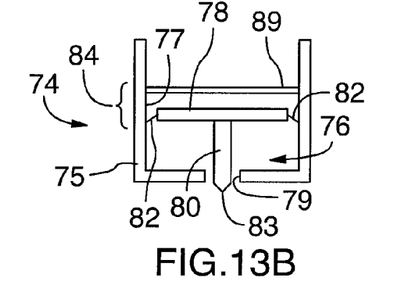
FIG. 13B, in a schematic view, illustrates the softness sensor shown in FIG. 13A, the softness sensor being shown in a deformed configuration.
Figure 13C:
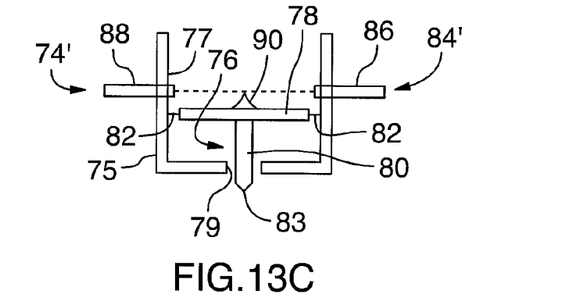
FIG. 13C, in a schematic view, illustrates a softness sensor in accordance with yet another embodiment of the present invention.

Referring to FIGS. 13A, there is shown an alternative deformable section 74. The deformable section 74 is shown uncoupled from a force sensor, but the deformable section 74 is usable with force sensors similarly to the way in which the above described deformable sections 29, 29' and 29" are. In FIG. 13A, the deformable section 74 is shown in the undeformed configuration. In FIG. 13C, the deformable section 74 is shown in the deformed configuration.

The deformable section 74 includes a deformable section base 75 defining a cavity 77. An aperture 79 lead into the cavity 77. An indentor 76 is received in the cavity 77 so as to be movable relatively thereto. The indentor 76 protrudes from the cavity 77 through the aperture 79. The indentor 76 is attached to the deformable section base 75 through substantially resiliently deformable elements 82. For example, the substantially resiliently deformable elements 82 are springs.

The indentor 76 includes an indentor base 78 and an indentor shaft 80 extending from the indentor base 78 and protruding outwardly from the deformable section base 75 through the aperture 79. The indentor shaft 80 defines a distal tip 83 substantially opposed to the indentor base 78. The distal tip 83 is the portion of the indentor 76 that abuts against an object for which softness is to be determined. The shape and dimensions of the indentor shaft 80 are selected according to the type of object 12 for which softness is determined. The indentor base 78 is attached to the substantially resiliently deformable elements 82 so as to mount the indentor 76 inside the cavity 77.

The deformable section 74 is operatively coupled to a deformation sensor 84 for sensing deformations of the deformable section 74. For example, the deformation sensor 84 includes an electrode 89 provided in a substantially parallel and spaced apart relationship relatively to the indentor base 78 and fixed with respect to the deformable section base 75, and the indentor base 78 is conductive, thereby forming another electrode. In this example, considering a capacitance between the indentor base 78 and the electrode 89 provides the distance between the indentor base 78 and the electrode 89. Since movements of the indentor 76 relatively to the deformable section base 75 are determined in this manner, deformations of the deformable section 74 are provided.

When the distal tip 83 and the portion of the deformation section base 75 substantially adjacent to the aperture 79 are pressed against a relatively soft object, the distal tip 83 will only be partially retracted towards the cavity 77 and a distance between the indentor base of 78 and the electrode 89 will be substantially similar in the deformed configuration and in the undeformed configuration. However, if the distal tip 83 is pressed against a relatively hard object, the indentor 76 will almost and entirely retract into the cavity 77 and the distance between the electrode 89 and the indentor base 78 will be relatively small. Typically, the depth of penetration of the distal tip 83 is independent or only weakly dependent on the load applied onto the object 12 by these two components.

As shown in FIG. 13C, in some embodiments of the invention, an alternative deformation sensor 84' is used in an alternative deformable section 74'. The deformation sensor 84' uses a light source 86 and a light detector 88 located substantially in register with the light source 86. A tapered element 90 is affixed to the indentor base 78 substantially opposed to the indentor shaft 80 so as to intercept, at least in part, the light coming from the ligh source 86 when the deformation sensor 84' is in the deformed configuration. The tapered element 90 tapers in a direction leading substantially away from the indentor shaft 80. The amount of light intercepted by the tapered element 90 depends on the deflection of the indentor 76 when abutted against the surface.

In some embodiments of the invention, a temperature sensor is provided on a grasper or any other device used with the proposed softness sensors 10, 10' and 10". The measured temperature information can be transmitted remotely to a temperature display device, including for example thermocoolers, such as Peltier devices, or a heating element. Any number of temperature display elements can be provided. Therefore, spatial and temporal temperature information can be readily transmitted remotely. Such information is useful, for example, in the case of medical applications in which diseased tissue is cooler or warmer than adjacent tissues. It should be notes that temperature differences can easily be amplified in the display device to facilitate temperature detection by an intended user of the temperature display device.

Although the present invention has been described hereinabove by way of preferred embodiments thereof, it can be modified, without departing from the spirit and nature of the subject invention as defined in the appended claims.

What is claimed is:

1. A sensing element for sensing the softness of an object by abutting said sensing element against said object and biasing said sensing element toward said object with a biasing force, said sensing element comprising:
    a deformable section, said deformable section defining a deformable section contact surface, said deformable section contact surface being deformable between an undeformed configuration and a deformed configuration, said deformed configuration being achievable when said deformable section contact surface is abutted against and biased toward said object;
    a deformation sensor operatively coupled to said deformable section for sensing a deformation of said deformable section contact surface between said deformed and undeformed configurations; and
    a force sensor operatively coupled to said deformable section for sensing said biasing force exerted onto said deformable section contact surface by said object when said deformable section contact surface is biased toward said object with said biasing force;
    wherein said biasing force and said deformation are sensed respectively by said force sensor and said deformation sensor independently from each other.

2. A sensing element as defined in claim 1, further comprising
    a base; and
    a spacing element extending substantially away from said base;
    said deformable section being supported by said spacing element in a substantially spaced apart relationship relatively to said base.

3. A sensing element as defined in claim 2, wherein said deformable section contact surface and said base are substantially parallel to each other.

4. A sensing element as defined in claim 2, wherein said deformation sensor includes a piezoelectric material operatively coupled to said deformable section for producing an electrical signal upon a deformation of said deformable section contact surface between said deformed and undeformed configurations.

5. A sensing element as defined in claim 2, wherein said deformation sensor includes a capacitor operatively coupled to said deformable section and to said base for producing an electrical signal upon a deformation of said deformable section contact surface between said deformed and undeformed configurations.

6. A sensing element as defined in claim 5, wherein said capacitor includes a first metal plate secured to said base and a second metal plate secured to said deformable section, said first and second metal plates being substantially in register with each other.

7. A sensing element as defined in claim 6, wherein said first and second metal plates are located between said deformable section and said base.

8. A sensing element as defined in claim 2, wherein said force sensor is mechanically coupled to said spacing element for sensing a force exerted on said spacing element when said deformable section contact surface is abutted against and biased toward said object.

9. A sensing element as defined in claim 8, wherein said force sensor includes a piezoelectric material operatively coupled to said spacing element for producing an electrical signal upon a force being exerted on said spacing element.

10. A sensing element as defined in claim 9, wherein said piezoelectric material is provided between said base and said spacing element.

11. A sensing element as defined in claim 1, further comprising
    a base; and
    a pair of spacing elements extending substantially away from said base and supporting said deformable section in a substantially spaced apart relationship relatively to said base;
    said deformable section contact surface extending between said spacing elements.

12. A sensing element as defined in claim 1, further comprising
    a harder material, said harder material defining a recess extending thereinto;
    said deformable section including a softer material substantially filling said recess, said softer material being substantially more deformable than said harder material when said deformable section and said harder material are simultaneously abutted against and biased toward said object.

13. A sensing element as defined in claim 12, wherein said force sensor includes a piezoelectric material mechanically coupled to said harder material and to said deformable section for sensing forces exerted onto said softer material and said harder material when said softer material and said harder material are simultaneously abutted against and biased toward said object.

14. A sensing element as defined in claim 12, wherein said harder material and said deformable section together define an abutment surface for abutting against said object, said sensing element comprising a sheet of piezoelectric material mechanically coupled to both said softer material and said harder material substantially opposed to said abutment surface.

15. A sensing element as defined in claim 14, wherein:
said deformation sensor includes a deformation sensor electrode electrically coupled to said sheet of piezoelectric material for receiving electrical signals from said sheet of piezoelectric material when a force is exerted onto said softer material; and
said force sensor includes a force sensor electrode electrically coupled to said sheet of piezoelectric material for receiving electrical signals from said sheet of piezoelectric material when a force is exerted onto said harder material;
said force sensor and deformation sensor electrodes are electrically insulated from each other.

16. A softness sensor, said softness sensor including a plurality of sensing elements as defined in claim 1, said plurality of sensing elements being distributed over a predetermined sensing surface.

17. A softness sensor as defined in claim 16, wherein said predetermined sensing surface is substantially planar.

\* \* \* \* \*